(12) United States Patent
Zallone et al.

(10) Patent No.: US 7,084,174 B2
(45) Date of Patent: Aug. 1, 2006

(54) ADMINISTRATION OF ISOVALERYL L-CARNITINE TO STIMULATE OSTEOBLASTIC ACTIVITY

(75) Inventors: Alberta Zallone, Bari (IT); Aleardo Koverech, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 11/032,019

(22) Filed: Jan. 11, 2005

(65) Prior Publication Data

US 2005/0143458 A1 Jun. 30, 2005

Related U.S. Application Data

(62) Division of application No. 10/470,158, filed as application No. PCT/IT01/00614 on Dec. 4, 2001, now Pat. No. 6,906,102.

(30) Foreign Application Priority Data

Dec. 21, 2000 (IT) .......................... RM2000A0688

(51) Int. Cl.
*A61K 31/205* (2006.01)
(52) U.S. Cl. ...................................................... 514/556
(58) Field of Classification Search ................. 514/556
See application file for complete search history.

(56) References Cited

FOREIGN PATENT DOCUMENTS

| WO | WO 98/01128 | 1/1998 |
| WO | WO98/46233 | 10/1998 |
| WO | WO 99/66913 | 12/1999 |

*Primary Examiner*—Phyllis G. Spivack
(74) *Attorney, Agent, or Firm*—Nixon & Vanderhye P.C.

(57) ABSTRACT

A method of stimulating osteoblastic activity comprising administering isovaleryl L-carnitine is disclosed.

5 Claims, 3 Drawing Sheets

ADMINISTRATION OF ISOVALERYL L-CARNITINE TO STIMULATE OSTEOBLASTIC ACTIVITY

CROSS REFERENCE TO RELATED APPLICATIONS

This application is a divisional of application Ser. No. 10/470,158 filed Jul. 24, 2003, now U.S. Pat. No. 6,906,102, which in turn is a US national phase of international application PCT/IT01/00614 filed Dec. 4, 2001 which designated the U.S.

The present invention relates to the use of isovaleryl L-carnitine for the preparation of a medicament for the prevention and cure of fractures.

Aged people or people which are in post-menopause are subjected to fractures due to the fragility of the bone caused by osteoporosis.

The hospitalisation period of patients with bone fractures, which may last some day or some months, depends from the type of fracture, the age, and from the general conditions of the patients.

The convalescence period depends on the gravity of the pathology. At the end of this period patients come back to the hospital for the radiographic controls of the bony callus formation.

Unfortunately not all patients present the same degree of recovery, in fact some of them present a minor, some time a complete lack of bony callus formation. Because of these events patients are obliged to remain inactive for a further period of time, with a loss of working day and an increases of the hospital expenses.

To date exist few specific therapeutical compounds which act directly on the bone cells, the osteoblasts, favouring in a specific way their propagation with formation of bony callus and wound healing.

In the orthopaedic section of the hospital, as adjuvant therapy of the fractures are used calcitonine or alendronates, drugs specific for the prevention of the post-menopausal osteoporosis, eventually in combination with vitamins, particularly with vita D and mineral salts, which act limiting the osteoclastic activity.

Therefor, the discovery of new drugs which exert their action directly on the osteoblasts and are capable both to support their multiplication and the bony callus formation, and to decrease the recovering period, would have a beneficial effect on the patients.

Considering the relevant number of patients involved, it is evident both the socio-economics benefit obtainable, reducing the hospital expenses, increasing the working day dog the year, and particularly improving the quality life of the patients.

Is therefore the scope of the present invention to furnish a drug, which overcoming the drawbacks and the unsatisfactory efficacy of the therapeutical compounds used to date, is capable to limits the osteoclastic activity accelerating the formation of bony matrix (stimulating the osteoblastic activity) and is an useful agent for the prevention and treatment of fractures.

Compounds useful for the cure of fractures are already known.

WO 98/46233 describes a pharmaceutical compositions comprising an alkanoyl L-carnitine in combination with the dehydroepiandrosterone (DHEA) or the dehydroepiandrosterone sulphate (DHEA-S) capable to stimulate the multiplication and growth of the osteoblast.

WO 99/66913 describes compositions useful for the treatment of the osteoporosis and menopausal syndromes which comprise propionyl L-carnitine in combination with 4'-5,7-trihydroxiflavone.

The patent FR 2765804 describes compositions useful for the treatment of osteoporosis containing calcium pidolate, calcium carbonate, and carnitine.

WO 98/01128 describes the use of acetyl L-carnitine, isovaleryl L-carnitine and propionyl L-carnitine for increasing the IGF-1 levels for the treatment and prevention of cytological disorders and pathologies related to IGF 1.

WO 95/05168 describes an oral medicament at controlled release comprising carnitine, which does not causes gastrointestinal irritation, for the treatment of the osteoporosis.

In Journal of Pharmaceutical Sciences Vol. 84; No 4; April 1995 is described the use of long chain acyl carnitine ester in racemic form (palmitoyl-carnitine, miristoyl-carnitine and lauroyl-carnitine), as useful agent for the prevention of the osteoporosis.

In "Comptes rendus des seances de la Société de Biologie. Seance du 27 Juin 1964.—Tome CLVIII, n 6, 1964, p. 1410" is reported that in rat the use of D,L-carnitine increases the bone calcium.

In The Journal of Rheumatology 1999, 26; 2229–32 is described the use of carnitine, in subject adult, for the treatment of the hip fracture.

In Revue Agressologie 1963—IV., 4, is described the use of carnitine during the growth or following fractures.

In Gerontologist, (9), 32–33, 1992 is reported that in mice treated with L-carnitine increase the production of osteocalcine (index of better calcification), while in the same animals the treatment with acetyl L-carnitine reduces the production of this marker during the formation of the bone matrix.

None of the above cited publications teach or suggest the use of isovaleryl L-carnitine for the preparation of a medicament for the treatment of fractures.

Moreover, the cited publication on Gerontologist gives a severe technical prejudice on the use of a short chain alkanoyl L-carnitines for promoting the production of bone matrix, in fact it is reported that acetyl L-carnitine to reduces the production of osteocalcine.

It has surprisingly been found that isovaleryl L-carnitine promotes the formation and proliferation of osteoblasts and is a therapeutic agent useful for the prevention and treatment of fractures during post-menopausal osteoporosis or secondary to elderly.

The experimental data, in the following reported, show that the compound according to the invention promotes cells proliferation and collagen production in human osteoblastic cells in vitro. In fact, isovaleryl L-carnitine shows to be more active than L-carnitine, or as active as, but a doses less than 10 or 20 times, respect to L-carnitine.

Is therefore object of the present invention the use of isovaleryl L-carnitine or a pharmacological acceptable salt thereof, for preparing a medicament useful for increasing the healing of fractures.

For pharmaceutically acceptable salt of isovaleryl L-carnitine is intended any salts of this with an acid which does not give rise to undesirable toxic or side effects.

This acids are well known to the experts in pharmacy and pharmaceutical technology.

Non-limiting examples of suitable salts include the chloride, bromide, orotate, acid aspartate, acid citrate, magnesium citrate, acid phosphate, fumarate, acid fumarate, magnesium fumarate, lactate, maleate, acid maleate, mucate, acid oxalate, pamoate, acid pamoate, acid sulphate, glucose phosphate, tartrate, acid tartrate, magnesium tartrate, 2-amino etanesulfonate, magnesium 2-amino etanesulfonate, coline tartrate and trichloroacetate.

Preferred is isovaleryl L-carnitine fumarate.

The compound according to the present invention can be administered to patients in need, either alone or in concomitance with vitamins, mineral salts and/or other known drugs useful for the treatment of fractures during osteoporosis.

The following example illustrate the invention.

EXAMPLE

Preparation of the Human Osteoblasts

The differentiated human osteoblasts were prepared starting from bone fragments obtained during surgical operation following the procedure described in Calcif. Tissue Int. 62: 362–365, 1998; and in Calcif. Tissue Int. 37: 453–460, 1985.

In short, bone fragments were undertaken to enzymatic digestion with collagenase (1 mg/ml) diluted in phosphate buffer in order to remove fibroblasts, haematic endothelial cells or bone marrow cells, if any.

The fragments so cleaned were maintained in culture in presence of a medium containing 20% of foetal calf serum (FCS) to obtain osteoblasts population for explant.

The cells so obtained were characterised to verify their osteoblastic phenotype then used for the experiments.

Cellular Proliferation Test

The cellular proliferation test was done growing the cells in 96 well plates, in medium without FCS, and with bovine serum albumin (BSA).

The cells were exposed to increasing doses of L-carnitine fumarate and isovaleryl L-carnitine fumarate. The positive control group was constituted by cells growing in presence of FCS (15%).

Every 24 ore, for 5 days, samples from plates in culture were fixed with a solution of paraformaldehyde at 3%, the cells were stained with crystal-violet at 0.5%, washed to eliminate the excess of stain and a solution of sodium citrate 0.1 M in ethanol was added. The number of the cells contained in the wells was evaluated by colorimetric test at 540 nm.

Figure 1:
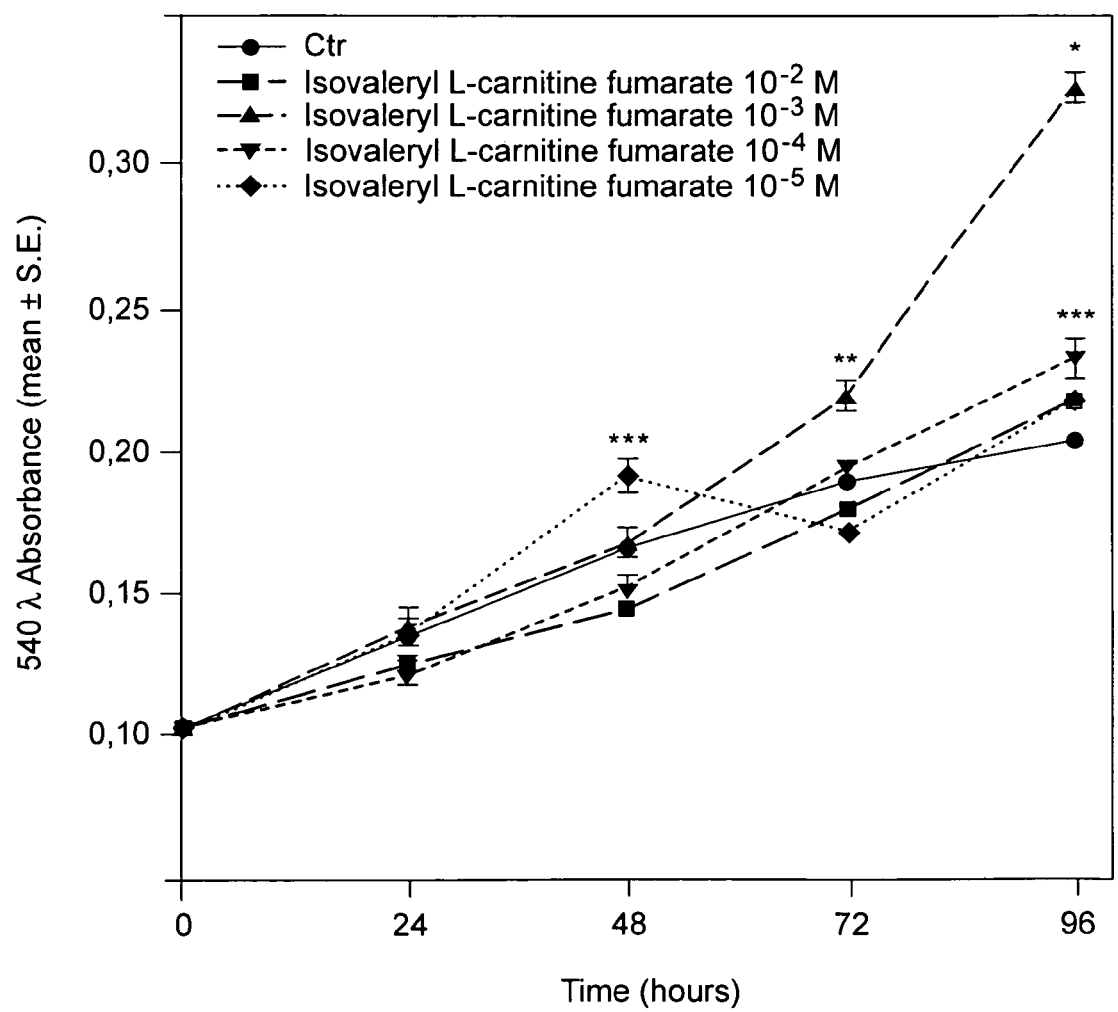
FIG. 1 depicts osteoblastic cell proliferation following the administration of isovaleryl L-carnitine.

The results obtained, reported in FIG. 1, shows that isovaleryl L-carnitine fumarate promotes cells proliferation.

Figure 2:
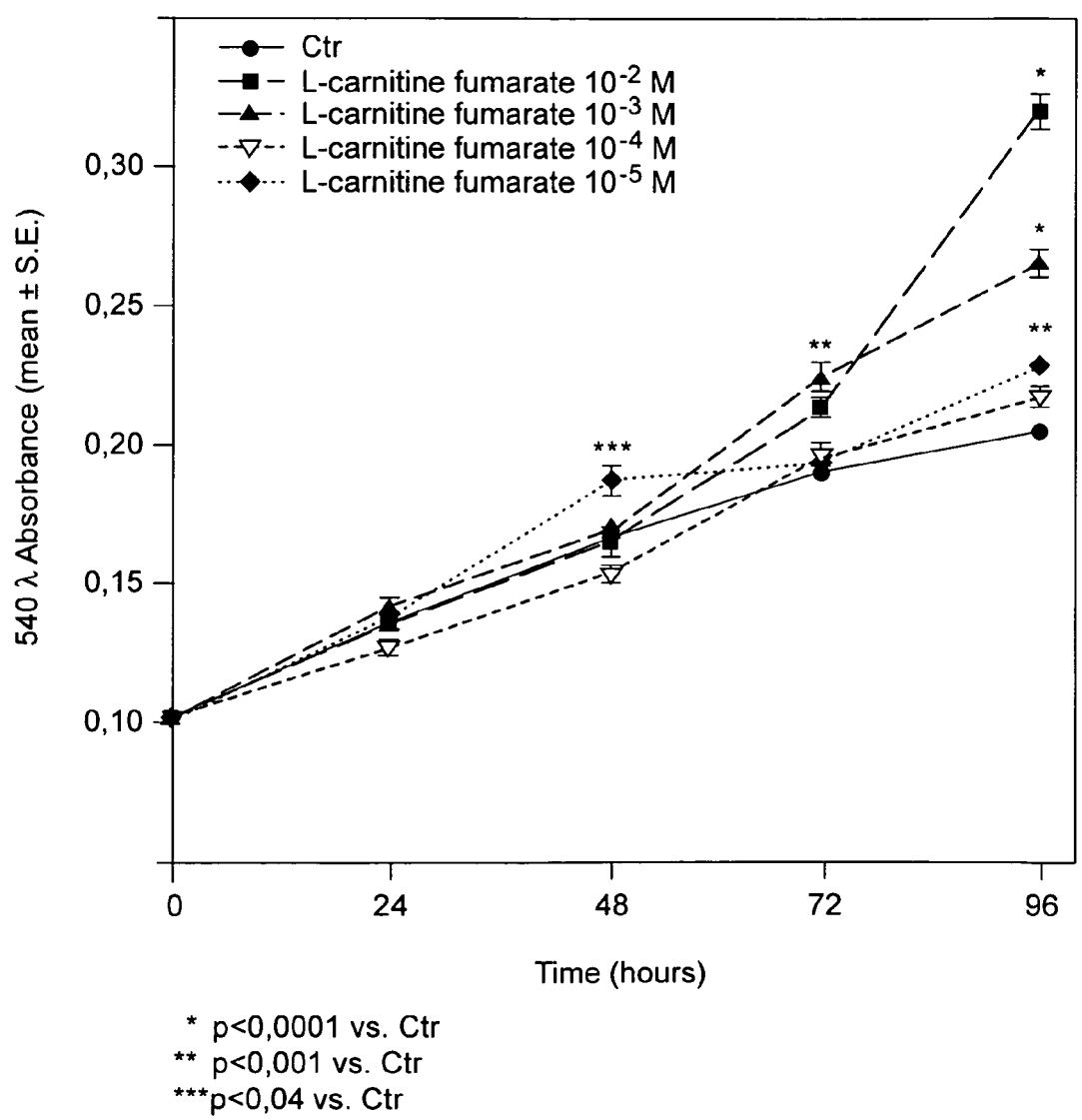
FIG. 2 depicts osteoblastic cell proliferation following the administration of L-carnitine fumarate.

Moreover, the results obtained reported in FIG. 1 (isovaleryl L-carnitine fumarate) in comparison with the results reported in FIG. 2 (L-carnitine fumarate) shown that isovaleryl L-carnitine fumarate induces cells proliferation (FIG. 1) in a more potent way, if compared with the cells proliferation induced by L-carnitine fumarate (FIG. 2).

In fact, it is worthy of note that in FIG. 1 isovaleryl L-carnitine fumarate at a dose ($10^{-3}$ M) 10 times lower than that of L-carnitine fumarate ($10^{-2}$ M) has the same cellular proliferation activity compared to the activity of L-carnitine fumarate (FIG. 2). The statistical analysis of the results was made using the Student "t" test.

Production of Collagen by Incorporation of $^3$H-Proline

The collagen production represents a method for the evaluation of the osteoblast activity.

This production was evaluated on semiconfluent cells grown on 24 wells plates, in medium without serum (FCS) containing 1 µCi/well of $^3$H-proline, both in the wells of the control and in the wells where were present the tested compounds. After 4 hours of incubation in presence of the tracer the cells were lysed and undertaken to an extraction procedure (Journal of Bone and Mineral Research, 2000; Vol. 15(2); 188–97). The cells were washed with phosphate buffer (PBS) dissolved in 0.5 ml/well of sodium dodecyl sulphate at 10% and undergone to precipitation for 30 minutes at 4° C. by the addition of sulphate trichloroacetic acid at 3%. The radioactivity of the cells, as index of the cells collagen synthesis, was evaluated with a beta-counter.

Figure 3:
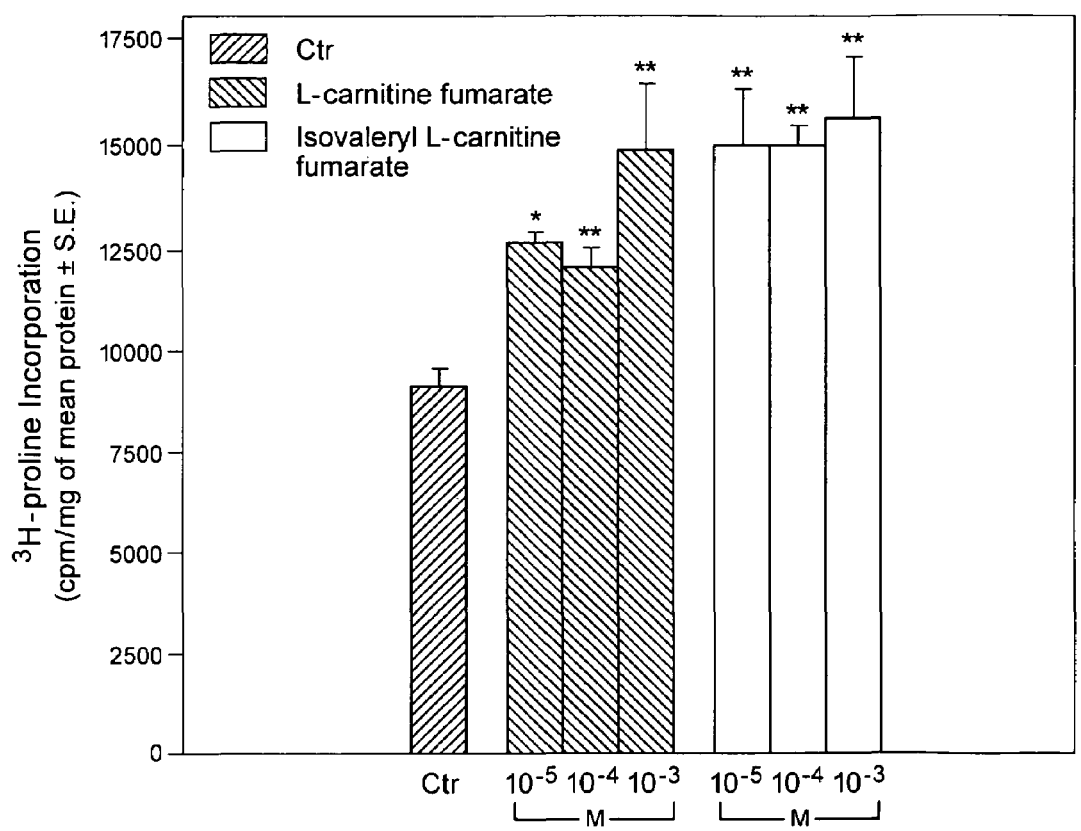
FIG. 3 depicts $^3$H-proline incorporation as a measure of collagen production.

The results obtained reported in FIG. 3 shown that isovaleryl L-carnitine fumarate increases the production of collagen in an higher way respect to the control sample, in which the tested compound was absent.

Moreover, the results obtained reported in FIG. 3 shown that isovaleryl L-carnitine fumarate has a favouring activity for the production of collagen in a significant way respect to the same doses of L-carnitine fumarate. The statistical analysis of the results was made using the Student "t" test.

As above mentioned, the results obtained shown that the compound according to the present invention promotes in a statistical significant way the proliferation and the collagen production in human osteoblastic cells in vitro respect to the control samples, in which said compounds was absent. Moreover, isovaleryl L-carnitine shows to be more active in some experiments, and as active as, at doses at least 10 times lower, also respect to the reference compound (L-carnitine).

The statistical analysis of all the results was made using the Student "t" test.

The amount of the drug to be administered to patients in need will be decided by the physician on the base of the age, weight and general conditions of the patient.

However, the unitary dosage to be administered will be about 0.5–3 g/day, preferably 1–2 g/day, in solid form, powder, granular or liposomic in pills, capsules, granulates, powder, vials for oral, parenteral, rectal or topic use.

These administration forms may further contain vitamins, mineral salts, and/or other known drugs useful for the treatment of the osteoporosis and fractures during osteoporosis.

The invention claimed is:

1. A method of stimulating osteoblastic activity to reduce the incidence of bone fractures consisting essentially of administering to a subject an effective amount of isovaleryl L-carnitine of a pharmaceutically acceptable salt thereof.

2. The method according to claim 1 in which the pharmaceutically acceptable salt is selected from the group consisting of chloride, chloride, bromide, orotate, acid aspartate, acid citrate, magnesium citrate, acid phosphate, fumarate, acid fumarate, magnesium fumarate, lactate, maleate, acid maleate, mucate, acid oxalate, pamoate, acid pamoate, acid sulphate, glucose phosphate, tartrate, acid tartrate, magnesium tartrate, 2-amino ethanesulfonate, magnesium 2-amino ethanesulfonate, choline tartrate and trichloroacetate.

3. The method according to claim 1, in which the pharmaceutically acceptable salt is fumarate.

4. The method according to claim 1, in which the amount of isovaleryl L-carnitine administered is 0.5 to 3 grams per day.

5. The method according to claim 4, in which the amount of isovaleryl L-carnitine administered is 1 to 2 grams per day.

* * * * *